United States Patent
Rao (10) Patent No.: US 10,799,292 B2
(45) Date of Patent: Oct. 13, 2020

(54) HIGH POWER TUNABLE OPTICAL PARAMETRIC OSCILLATOR FOR SELECTIVE PHOTOTHERMOLYSIS LASER SURGERIES

(71) Applicant: Bin Rao, Saint Louis, MO (US)

(72) Inventor: Bin Rao, Saint Louis, MO (US)

(73) Assignee: Bin Rao, Saint Louis, MO (US)

( * ) Notice: Subject to any disclaimer, the term of this patent is extended or adjusted under 35 U.S.C. 154(b) by 154 days.

(21) Appl. No.: 15/970,910

(22) Filed: May 4, 2018

(65) Prior Publication Data

US 2019/0336213 A1 Nov. 7, 2019

(51) Int. Cl.
*H01S 3/10* (2006.01)
*A61B 18/20* (2006.01)
(Continued)

(52) U.S. Cl.
CPC ............ *A61B 18/203* (2013.01); *H01S 3/005* (2013.01); *H01S 3/094* (2013.01); *H01S 3/10053* (2013.01); *H01S 3/1611* (2013.01); *H01S 3/1643* (2013.01); *H01S 3/2308* (2013.01); *A61B 2017/0019* (2013.01);
(Continued)

(58) Field of Classification Search
CPC ................. A61B 18/203; A61B 18/22; A61B 2018/00005; A61B 2018/00458; A61B 2018/2261; A61B 18/00452; A61B 2017/00172; A61B 2017/0019; A61B 2018/00702; A61B 2018/00761; A61B 18/20; A61N 2005/067; H01S 3/094; H01S 3/10053; H01S 3/2308; H01S 3/005;
(Continued)

(56) References Cited

U.S. PATENT DOCUMENTS 4,303,343 A * 12/1981 Patel .................. G01N 21/1702
250/351
5,117,126 A 5/1992 Geiger
(Continued)

FOREIGN PATENT DOCUMENTS

WO WO2013033145 A1 3/2013

OTHER PUBLICATIONS

Barua et al., "Laser-tissue interaction in tattoo removal by Q-switched lasers," J Cutan Aesthet Surg 8, 5-8(2015).
(Continued)

*Primary Examiner* — Amy R Weisberg (57) ABSTRACT

A laser with a wide continuous wavelength tuning range is desirable for optimized selective photothermolysis (SP) laser surgeries that treat light-absorptive lesions and unwanted pigments in human tissue with minimal collateral damages. However, current SP laser surgical systems are limited to a few lasing lines including 1064 nm by Nd:YAG, 755 nm by Alexandrite, 694 nm by Ruby, and 532 nm by second harmonic generation of 1064 nm. This invention discloses techniques to implement a high power, tunable optical parametric oscillator (OPO) system for demanding SP applications such as laser tattoo removal. In addition to wavelength tuning, the OPO laser system's output pulse energy, pulse duration, and pulse-train duration are also adjustable by tuning the pump laser pulse energy, pump laser pulse duration, and pump laser pulse-train duration for optimizing SP laser surgical outcomes.

13 Claims, 6 Drawing Sheets

(51) Int. Cl.
  *H01S 3/094* (2006.01)
  *H01S 3/23* (2006.01)
  *H01S 3/00* (2006.01)
  *H01S 3/16* (2006.01)
  *A61B 18/22* (2006.01)
  *A61B 18/00* (2006.01)
  *A61B 17/00* (2006.01)

(52) U.S. Cl.
  CPC ............. *A61B 2017/00172* (2013.01); *A61B 2018/00452* (2013.01); *A61B 2018/00702* (2013.01); *A61B 2018/00761* (2013.01); *A61B 2018/2261* (2013.01)

(58) Field of Classification Search
  CPC .... H01S 3/1611; H01S 3/1643; H01S 3/2383; H01S 3/0092; G02F 1/39
  See application file for complete search history.

(56) References Cited

U.S. PATENT DOCUMENTS

| | | | |
|---|---|---|---|
| 5,383,200 A * | 1/1995 | Barrett | G02B 23/12 250/214 VT |
| 5,390,211 A | 2/1995 | Clark | |
| 5,619,517 A | 4/1997 | Dixon | |
| 5,759,200 A * | 6/1998 | Azar | A61B 18/203 606/10 |
| 5,772,656 A * | 6/1998 | Klopotek | A61F 9/00804 219/121.6 |
| 5,840,023 A * | 11/1998 | Oraevsky | A61B 5/0095 600/407 |
| 5,847,861 A * | 12/1998 | Kafka | G02F 1/39 359/330 |
| 5,879,346 A | 3/1999 | Waldman | |
| RE36,634 E | 3/2000 | Ghaffari | |
| 6,101,023 A * | 8/2000 | Meyer, Jr. | G02F 1/39 359/330 |
| 6,270,492 B1 | 8/2001 | Sinofsky | |
| 6,273,883 B1 | 8/2001 | Furumoto | |
| 6,309,352 B1 * | 10/2001 | Oraevsky | A61B 5/0095 367/7 |
| 6,498,942 B1 * | 12/2002 | Esenaliev | A61B 5/0095 600/310 |
| 6,522,402 B1 * | 2/2003 | Wang | G01J 3/42 356/326 |
| 6,542,767 B1 * | 4/2003 | McNichols | A61B 5/0008 600/407 |
| 6,554,825 B1 | 4/2003 | Murray | |
| 6,605,080 B1 * | 8/2003 | Altshuler | A61B 18/203 606/3 |
| 6,607,523 B1 | 8/2003 | Asah | |
| 6,683,894 B1 * | 1/2004 | Lee | H01J 49/164 372/10 |
| 6,723,090 B2 | 4/2004 | Altshuler | |
| 6,766,187 B1 | 7/2004 | Black | |
| 7,036,516 B1 | 5/2006 | Dees | |
| 7,179,253 B2 | 2/2007 | Graham | |
| 7,331,953 B2 | 2/2008 | Manstein | |
| 7,713,265 B2 | 5/2010 | Dunki-Jacobs | |
| 8,394,359 B1 | 3/2013 | O'Neil | |
| 10,359,400 B2 * | 7/2019 | Wang | A61B 5/0095 |
| 2002/0019625 A1 * | 2/2002 | Azar | A61B 18/203 606/9 |
| 2003/0103213 A1 * | 6/2003 | Adams | G01J 9/00 356/484 |
| 2004/0039379 A1 * | 2/2004 | Viator | A61B 18/203 606/9 |
| 2006/0004306 A1 * | 1/2006 | Altshuler | A61B 18/203 601/3 |
| 2006/0153254 A1 * | 7/2006 | Franjic | B23K 26/38 372/30 |
| 2006/0206103 A1 * | 9/2006 | Altshuler | A61B 18/203 606/9 |
| 2007/0159592 A1 * | 7/2007 | Rylander | A61B 5/0066 351/44 |
| 2008/0037595 A1 * | 2/2008 | Gankkhanov | G01J 3/10 372/3 |
| 2008/0058783 A1 * | 3/2008 | Altshuler | A61B 18/20 606/9 |
| 2008/0132886 A1 * | 6/2008 | Cohen | A61B 18/203 606/34 |
| 2008/0172047 A1 * | 7/2008 | Altshuler | A61B 5/441 606/9 |
| 2009/0069741 A1 * | 3/2009 | Altshuler | A61B 5/441 604/22 |
| 2009/0105588 A1 * | 4/2009 | Emelianov | A61B 5/4869 600/438 |
| 2009/0143773 A1 * | 6/2009 | Gosse | A61B 18/203 606/12 |
| 2009/0227997 A1 * | 9/2009 | Wang | A61B 18/24 606/10 |
| 2010/0021867 A1 * | 1/2010 | Altshuler | A61K 6/77 433/215 |
| 2010/0049180 A1 * | 2/2010 | Wells | A61N 5/0616 606/12 |
| 2010/0082019 A1 * | 4/2010 | Neev | A61B 18/203 606/9 |
| 2010/0324426 A1 * | 12/2010 | Tucek | A61B 5/0064 600/476 |
| 2011/0087202 A1 * | 4/2011 | Lewinsky | A61B 18/22 606/14 |
| 2012/0010603 A1 * | 1/2012 | Milner | A61B 5/0053 606/13 |
| 2012/0120466 A1 * | 5/2012 | Lee | H01S 3/06754 359/9 |
| 2012/0245571 A1 * | 9/2012 | Mordaunt | H01S 5/06825 606/4 |
| 2013/0166001 A1 * | 6/2013 | Fried | A61N 5/0622 607/89 |
| 2013/0345685 A1 | 12/2013 | Poran | |
| 2015/0211983 A1 * | 7/2015 | Speck | G02F 1/39 73/152.18 |
| 2015/0216420 A1 * | 8/2015 | Oraevsky | A61B 5/0095 600/440 |
| 2015/0272444 A1 * | 10/2015 | Maslov | A61B 5/0095 600/407 |
| 2016/0028210 A1 * | 1/2016 | O'Shaughnessy | G01N 21/645 372/34 |
| 2016/0334618 A1 * | 11/2016 | Hargis | G02B 26/0875 |
| 2017/0014186 A1 * | 1/2017 | Chen | A61B 5/4836 |
| 2017/0014317 A1 * | 1/2017 | Youngbull | A61K 8/19 |
| 2017/0176839 A1 * | 6/2017 | Nguyen | G02F 1/39 |
| 2017/0354464 A1 * | 12/2017 | Waisman | A61B 17/22 |
| 2018/0323571 A1 * | 11/2018 | Brown | H01S 3/1305 |
| 2019/0209376 A1 * | 7/2019 | Neev | A61F 9/00814 |
| 2019/0216542 A1 | 7/2019 | Rao | |
| 2019/0357976 A1 * | 11/2019 | Youngquist | A61N 5/0616 |

OTHER PUBLICATIONS

Bernstein, "Laser Tattoo Removal," Seminars in Plastics Surgery 21, 175-192(2007).
Ortiz et al., "Port-wine stain laser treatment and novel approaches," Facial Plast Surg 28, 611-620(2012).
Peach et al., "Colour shift following tattoo removal with Q-switched Nd-YAG laser (1064/532)," British Journal of Plastic Surgery 52,482-487(1999).
Wenzel, "Current concepts in laser tattoo removal," Skin Therapy Letter 15, 3-5(2010).
PrimoScan OPO data sheet [Retrieved on May 2, 2018]. Retrieved from the Internet: <URL:http://www.spectra-physics.com/products/high-energy-pulsed-lasers/primoscan-opo>.
BasiScan OPO dated sheet [Retrieved on May 2, 2018]. Retrieved from the Internet: <URL:http://www.spectra-physics.com/products/high-energy-pulsed-lasers/basiscan>.

* cited by examiner

HIGH POWER TUNABLE OPTICAL PARAMETRIC OSCILLATOR FOR SELECTIVE PHOTOTHERMOLYSIS LASER SURGERIES

CROSS-REFERENCE TO RELATED APPLICATIONS

None.

BACKGROUND OF THE INVENTION

This document relates to techniques and methods for selective photothermolysis (SP) laser surgeries.

SP, as described by Anderson and Parrish in a paper published by SCIENCE in 1983, utilizes short laser pulses to precisely control collateral thermal or mechanical damages around light-absorptive lesions without the need of aiming a laser micro-beam at surgical targets. A SP laser surgery has two distinct features, a large surgical area and a short surgical laser pulse that deposits most of the laser pulse energy into surgical targets. Thus non-surgical targets within a large surgical area remain healthy after SP while all surgical targets are damaged. Typical SP laser surgery examples include laser treatment of vascular malformations, some laser retinal photocoagulation surgeries, and some aesthetical laser surgeries such as laser tattoo removal. However, there is a big gap between the SP theory and SP laser surgery practices due to technical limitations. Most SP laser surgery systems are operating with non-optimized laser parameters and unsatisfactory SP laser surgical outcomes are direct results of non-optimized SP laser parameters. Techniques, apparatus and methods to optimize SP laser surgical outcomes including the addition of an ultrasonic detector in a SP laser surgical system using a tunable light source were disclosed in U.S. Ser. No. 15/881,748. It is desirable that such a tunable light source has not only wide wavelength tunability within visible and near infrared (VIS-NIR) range but also high power with a pulse energy of several hundred Milli-joules (mJ). However, it is challenging to achieve both in a tunable light source due to limitations of current laser techniques. This invention discloses techniques and methods to overcome the limitations of current laser techniques and enable demanding high power SP applications such as laser tattoo removal. The disclosed techniques and methods may also apply to other laser applications that requires high power.

BRIEF SUMMARY OF THE INVENTION

This document relates to techniques, apparatus and methods for optimized selective photothermolysis (SP) laser surgeries.

In one aspect, a high power tunable optical parametric oscillator system for SP laser surgeries comprises a pump laser that generates multiple high power, pulsed, pump laser beams; an optical parametric oscillator with multiple parallel optical parametric oscillator (OPO) modules pumped by the multiple pump laser beams, and multiple output beams whose lasing wavelengths are determined by phase-matching conditions of the OPO crystals within the OPO modules; a light delivery unit that assembles OPO output beams, adjusts diameters of OPO output beams, and directs OPO output beams to patient interface with an articulated arm or an optical light-guide including optical fibers; and a patient interface comprising a scattering medium that effectively combines multiple OPO output beams with high transmission through the scattering medium and disperses the combined laser energy on tissue surface. Such a high power tunable optical parametric oscillator system can be utilized to perform SP laser surgeries with known laser parameters.

In another aspect, a high power tunable optical parametric oscillator system for SP laser surgeries comprises a pump laser that generates multiple high power, pulsed, pump laser beams; an optical parametric oscillator with multiple parallel optical parametric oscillator (OPO) modules pumped by the multiple pump laser beams, and multiple output beams whose lasing wavelengths are determined by phase-matching conditions of the OPO crystals within the OPO modules; a light delivery unit that assembles OPO output beams, adjusts diameters of OPO output beams, and directs OPO output beams to patient interface with an articulated arm or an optical light-guide including optical fibers; and a patient interface comprising an acoustic detector for acquiring photoacoustic responses of tissue upon excitation by pulsed OPO output beams, and a scattering medium that effectively combines the multiple OPO output beams with high transmission through the scattering medium and disperses the combined laser energy on tissue surface. Such a high power tunable optical parametric oscillator system can be utilized to acquire optimal laser parameters and perform SP laser surgeries with optimal laser parameters.

DETAILED DESCRIPTION OF THE INVENTION

Selective photothermolysis (SP) utilizes short laser pulses to precisely target light-absorptive lesions with minimum collateral thermal or mechanical damages to surrounding healthy tissue. Major SP commercial applications include laser tattoo removal, laser treatment of vascular malformations and laser retinal photocoagulation.

Laser tattoo removal is usually performed with very short laser pulses in nanosecond or picosecond regime. Laser energy is transformed into both thermal energy and mechanical energy carried by the photoacoustic waves. In many cases, large laser pulse energy absorbed by pigmented particles may cause optical breakdown, plasma generation, chemical reactions between plasma and pigmented particles, cavitation and generation of acoustic shock-waves. These pigmented particles might be pyrolytically altered or shattered into smaller particles by the photoacoustic waves and acoustic shock-waves. Hosting cell necrosis and surround tissue damage might be induced thermally and mechanically during this process. In the end, the wound healing process might remove partial pigmented particles through rephagocytosis and alter the dermal scattering coefficients of the affected tissue, which might make the deeper pigmented particles less visible. A large number of tattoo inks of different colors with different light absorbing characteristics could be applied within human skin by tattoo artists. However, there are currently only a handful of laser wavelengths (for example, 694 nm ruby laser, 755 nm Alexandrite, 1064 nm Nd:YAG and 532 nm second harmonic generation of Nd:YAG) available in the market for laser tattoo removal. In addition, the tattoo-removal laser wavelength is selected based on the tattoo's color appearance to the naked eye instead of an optimal wavelength that damages pigmented lesions and protects nature chromophores in tissue to a maximum extent. The techniques, apparatus and methods disclosed in U.S. Ser. No. 15/881,748 addressed the problem of how to acquire optimal SP laser treatment parameters including wavelength selection. The problem to be addressed here is how to implement a high power tunable SP laser for demanding SP applications such as laser tattoo removal since such a laser does not exist so far. The solution to the problem could also apply to the laser treatment of vascular malformations wherein a number of discrete wavelengths (for example, 488/514 nm by Argon laser, 520/530 nm by Krypton laser, 532 nm by second harmonic generation of Nd:YAG laser, 578 nm by copper bromide/copper vapor laser, 585/595 nm by pulsed dye laser, 755 nm by Alexandrite laser, 800-940 nm by laser diode, and 1064 nm by Nd:YAG laser) are currently available for the photocoagulation of vascular lesions.

Both a wide wavelength tunability within the visible and near infrared (VIS-NIR) spectrum and a high power level with a pulse energy of several hundred Milli-joules (mJ) are required for demanding SP applications such as laser tattoo removal. A tunable lasers that fulfills both requirements can hardly be found in laser literature. Laser wavelength is determined by both the gain medium and wavelength selection mechanism in the laser cavity. The wavelength tuning range is determined by the spontaneous emission spectrum and the threshold condition of the laser cavity. Most solid state laser gain medium (for example, Ti:Sapphire 670-1070 nm, Cr:LiSAF 780-920 nm, Alexandrite 700-800 nm, and Cr:GSGG 700-900 nm) barely covers visible light range. Laser dyes (for example, Fluorescein-27 in Ethanol & water 541-571 nm, Pyrromethene-580 in Ethanol 547-581 nm, Rhodamine-6G 556-582 nm, Pyrromethene-597 558-587 nm, Sulforhodamine-B in Ethanol 585-600 nm, Rhodamine-B in Ethanol 588-614 nm, Rhodamine-101 in Ethanol 614-662 nm, DCM in Ethanol 595-665 nm, DCM in DMSO 616-690 nm, Pyridine-1 in Ethanol 667-720 nm, Pyridine-2 in Ethanol 691-751 nm, Styryl-8 in Ethanol 712-182 nm, Styryl-8 in DMSO 733-802 nm, Styryl-11 in Ethanol 758-826 nm, Styryl-9 in Ethanol 791-839 nm, Styryl-9 in DMSO 814-862 nm, LDS-867 in Ethanol 831-900 nm) do cover VIS-NIR range, but have a very limited wavelength tuning range for each dye. In order to achieve wide VIS-NIR wavelength tuning range, a number of switchable dye cells have to be utilized for both the oscillator stage and the laser power amplifier stage. It is imaginable that such a dye laser's dye circulator system alone would be very complicated and the operation and maintenance costs would be very high. Although there are studies on lasers with solid dyes, they are only suitable for low and medium power applications. Thus, a wide wavelength tuning range within VIS-NIR is extremely difficult to achieve with a traditional laser gain medium within a laser cavity.

Optical parametric oscillator (OPO) based on parametric down conversion process by non-linear OPO crystals has potential to generate widely-tuning laser wavelengths within VIS-NIR for SP. In the optical parametric down conversion process, a non-linear OPO crystal emits a signal photon of wavelength λs and an idle photon of wavelength λi when it is pumped by an excitation laser photon of wavelength λp. Both energy and momentum are preserved in the optical parametric down conversion process. The phase matching condition determines λs and λi. Adjusting phase matching conditions can effectively tune the output laser wavelength of OPO. The first commercial OPO device was introduced in early 1970s. However, the non-linear crystals in OPOs are easily damaged and that make OPOs less useful than tunable dye laser for almost 20 years before the discovery of damage-resistant nonlinear crystals with large nonlinear coefficients in the early 1990s. VIS-NIR OPOs are currently widely used in many applications due to its continuous, wide wavelength tuning capability. Although OPO seems simple and elegant, it is difficult to make high-power OPOs due to the potential damages to the OPO crystals, limited aperture size of OPO crystals, and high requirements on pump laser beam for high parametric conversion efficiency, especially the low pump beam divergence of 0.5-1 milliradian. For example, a low cost commercial OPO laser (basiScan-HE280 by Spectra Physics) only allows a maximum 280 mJ pump laser (355 nm) energy and generates a maximum signal output of 95 mJ. Another more advanced OPO (PrimoScan-BB750 OPO by Spectra Physics) delivers a maximum signal output of about 200 mJ with a 750 mJ pump laser (355 nm) energy and a large OPO crystal that accommodates 14 mm diameter beams. However, several hundred mJ of laser pulse energy is required by demanding SP applications such as laser tattoo removal. Thus, even one of the most powerful commercial OPOs (PrimoScan-BB750 OPO) might not satisfy demanding SP applications.

In summary, the prior art is deficient in high power, widely-tunable lasers for demanding SP applications such as laser tattoo removal. Both a VIS-NIR tunable dye laser and a VIS-NIR tunable OPO have similar low pump efficiencies and require high-power solid-state pump laser. Considering the wide wavelength tuning range of OPO and its simple and elegant structure, a VIS-NIR OPO should be a better solution for demanding SP applications than a VIS-NIR tunable dye laser when the OPO's power could satisfy SP applications. This invention discloses techniques and methods on how to implement a high power VIS-NIR OPO for demanding SP applications such as laser tattoo removal. Detailed descriptions of this invention are provided below.

Figure 1:
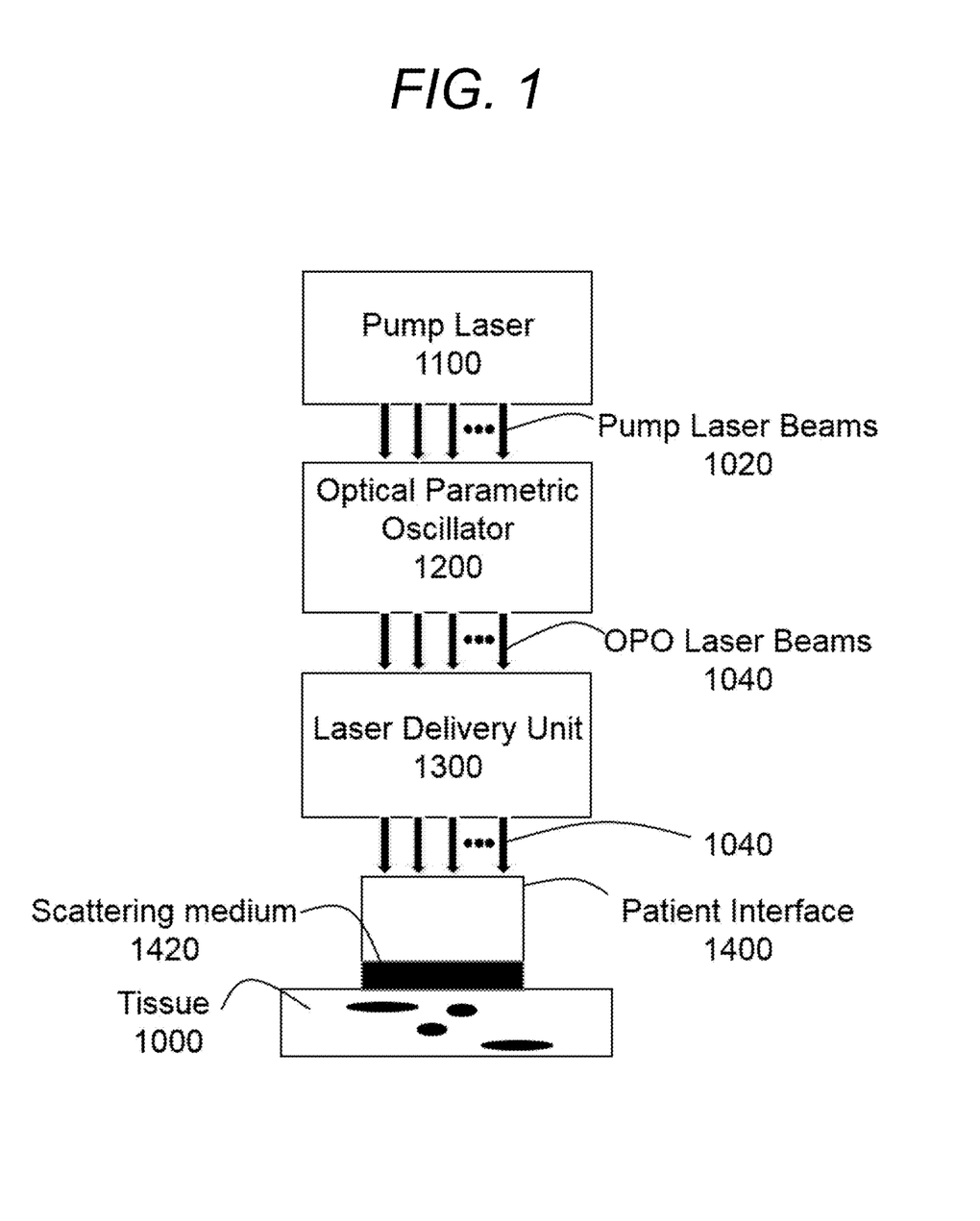
FIG. 1 shows an example of a high power tunable optical parametric oscillator with multiple output beams that are combined and dispersed on tissue surface by a scattering medium within a patient interface.

As an example, FIG. 1 shows an example of a high power, tunable optical parametric oscillator system wherein the generations of multiple output beams upon pumping by multiple pump beams, and the inclusion of a scattering medium in its patient interface differentiate it from a conventional tunable optical parametric oscillator in prior art of this invention. This high power, tunable optical parametric oscillator system comprises a high-power, solid state pump laser 1100 with multiple pump laser beams 1020; an optical parametric oscillator 1200 with multiple OPO laser beams 1040 as its output; a laser delivery unit 1300 that assembles multiple OPO laser beams 1040, adjusts diameters of the OPO laser beams 1040, delivers the OPO laser beams 1040 with an articulated arm or with an optical light-guide including optical fibers, and transmits the OPO laser beams 1040 through a patient interface 1400 comprising a scattering medium 1420 to a tissue 1000 surface; and a patient interface 1400 operable to be in contact with a tissue 1000 surface. The high power, tunable optical parametric oscillator system generates pulsed OPO laser beams that fulfill requirements of SP applications. For laser tattoo removal, the pulse duration of OPO laser beams is less than $10^{-7}$ seconds, or less than $10^{-8}$ seconds, or less than $10^{-9}$ seconds. For laser treatment of vascular malformations, the pulse duration or the pulse-train duration of OPO laser beams is longer than 1 millisecond. In order to avoid high power pump laser damages to the OPO crystal, this invention adopts a strategy that divides the high-power pump energy into multiple pump laser beams 1020 that pump multiple OPO crystals. This is the first characteristics of this invention. The spatially separated OPO output beams are combined and dispersed onto tissue surface by a patient interface comprising a scattering medium. This is the second characteristics of this invention. This invention provides hardware part of a tunable laser that serves as the tunable light source disclosed in U.S. Ser. No. 15/881,748. However, the operation methods of the high power tunable optical parametric oscillator system for SP applications are disclosed in U.S. Ser. No. 15/881,748. The pulse energy of OPO laser beams 1040 can be tuned by adjusting the pulse energy of pump laser 1100. And the pulse duration or pulse-train duration of OPO laser beams 1040 can be tuned by adjusting the pulse duration or pulse-train duration of the pump laser 1100 accordingly. The wavelength tuning of OPO laser beams 1040 is achieved by adjusting phase matching conditions of OPO crystals (not shown by FIG. 1) inside the optical parametric oscillator 1200. In the following paragraphs, detailed examples of the pump laser 1100, the optical parametric oscillator 1200, and the patient interface 1400 are disclosed.

Figure 2:
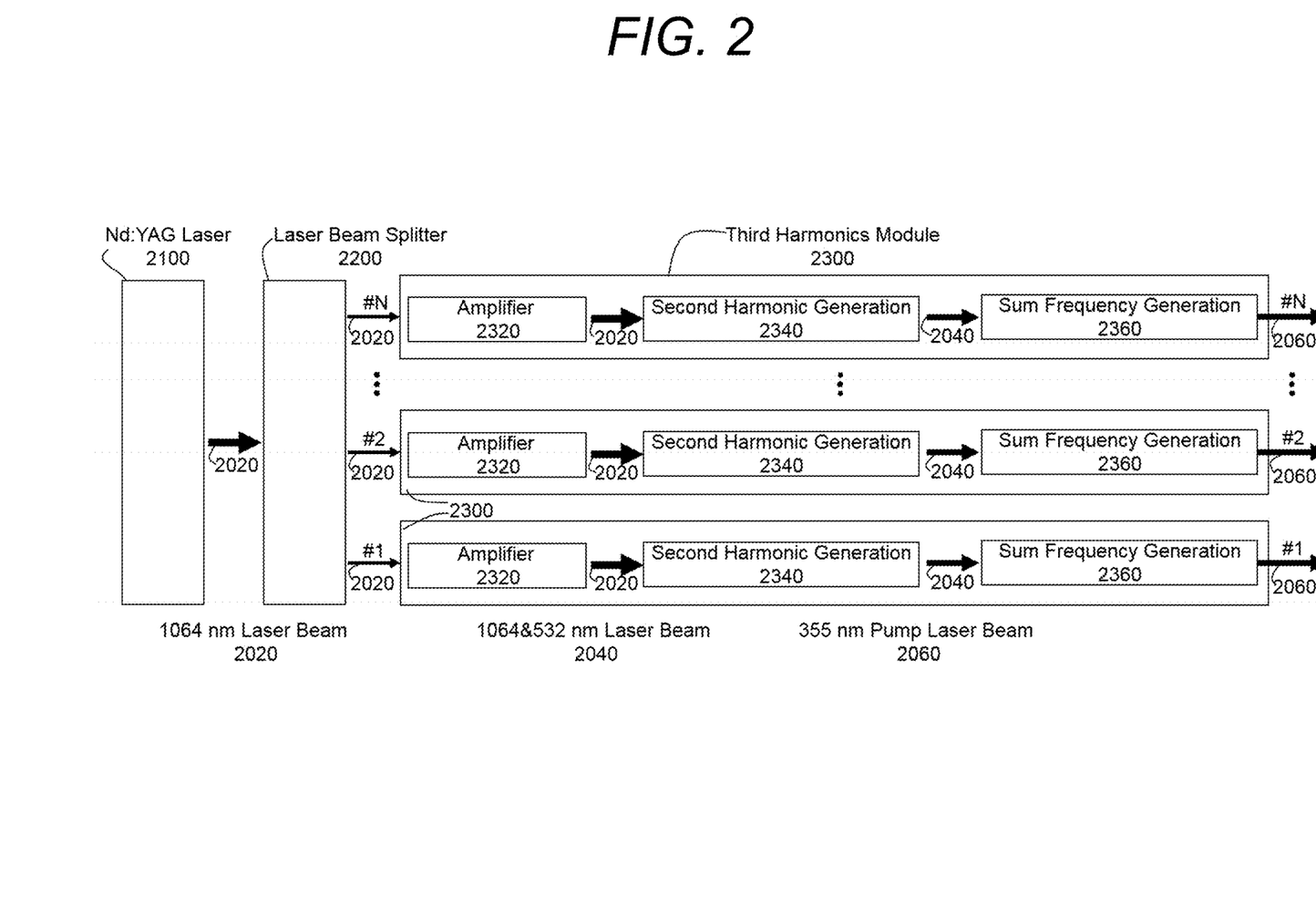
FIG. 2 show an example of pump laser that generates multiple 355 nm pump laser beams.

Solid state laser has become a mature technique that can be utilized to build the master oscillator of a high power pump laser with a "MOPA" (Master Oscillator Power Amplifier) structure. The master oscillator of the high power pump laser has only low to medium power, but high time and spatial coherence required by applications. It is the power amplifier after the master oscillator that achieves high power required by applications. Both the master oscillator and power amplifier can be pumped by flash-lamps, arc-lamps or laser diodes. FIG. 2 shows an example of a high power pump laser of 355 nm with multiple pump laser beams for pumping VIS-NIR OPO. The pump laser of this particular example has a pulse duration in nanosecond or picosecond regime for the laser tattoo removal application. A Nd:YAG lase 2100 serves as the main oscillator of the pump laser and generates a fundamental 1064 nm laser beam 2020 with a low-to-medium pulse energy, a narrow bandwidth, a low M2 factor and a low beam divergence. The 1064 nm laser beam 2020 is divided into multiple (from #1 to # N) 1064 nm laser beams 2020 for pumping multiple (from #1 to # N) third harmonic modules 2300 that generate multiple (#1 to # N) 355 nm pump laser beams 2060 for optical parametric down conversion. Within each third harmonic module 2300, the power of each input 1064 nm laser beam 2020 is amplified by an amplifier 2320 before sequentially pumping a second harmonic generation (SHG) 2340 unit and a sum frequency generation (SFG) 2360 unit for the generation of the 355 nm pump laser beam 2060. 1064 & 532 nm laser beams 2040 serve as inputs to the sum frequency generation (SFG) 2360 units. Depending on the specific SP applications, the SFG 2360 unit could be skipped when multiple pump laser beams are required at 532 nm instead of 355 nm, and the SHG 2340 unit could be further optimized to ~70% efficiency.

Figure 3:
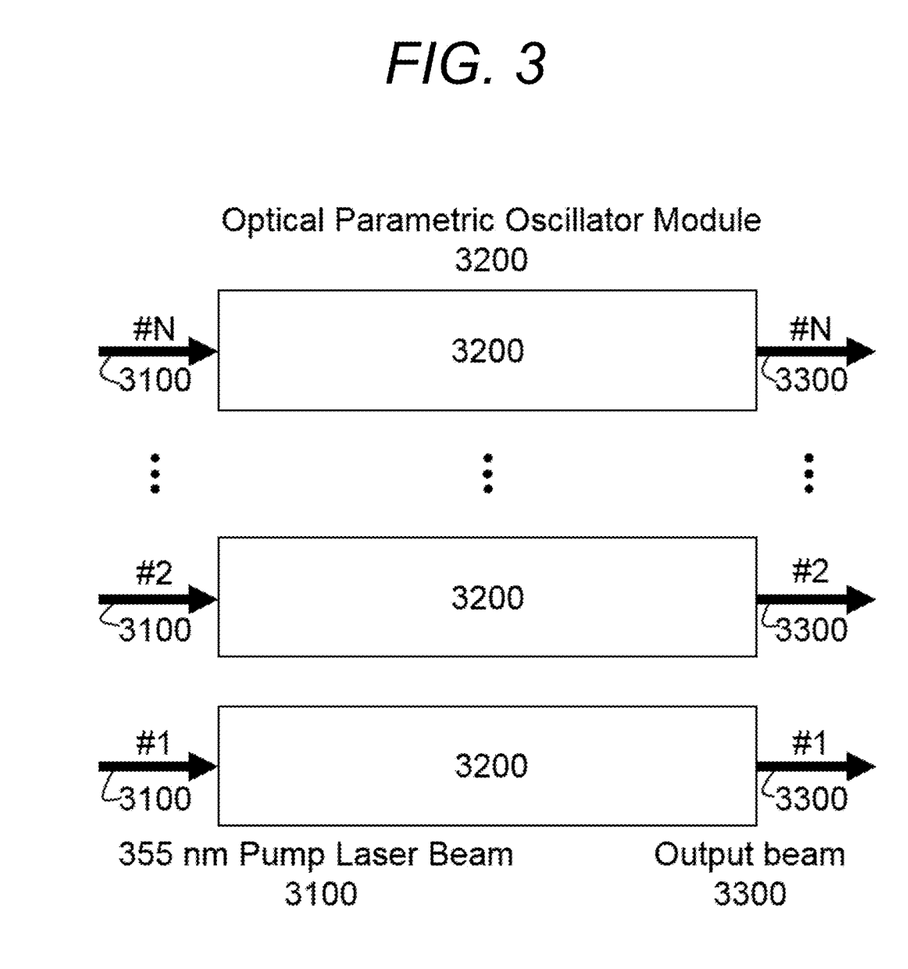
FIG. 3 shows an example of optical parametric oscillator that comprises multiple optical parametric oscillator modules and multiple output beams.

FIG. 3 shows an example of optical parametric oscillator that comprises multiple (from #1 to # N) optical parametric oscillator modules 3200 that convert 355 nm pump laser beam 3100 energy into output laser beam 3300 energy at a wavelength determined by phase matching conditions of the non-linear OPO crystals (for example, phase matching angle or temperature of the non-linear OPO crystals) inside the optical parametric oscillator module 3200. The optical parametric oscillator of this example has a pulse duration that is slightly shorter than the 355 nm pump laser beam 3100 because of a short period of time is required to build up optical parametric oscillation within the optical parametric oscillator cavity. Each optical parametric oscillator module could have its own oscillator cavity mirrors or share a pair of large cavity mirrors when a more compact design of the optical parametric oscillator is adopted. The multiple (from #1 to # N) output beams 3300 could be selectable between the OPO signal beams and OPO idler beams if it is desirable for the SP applications.

Figure 4:
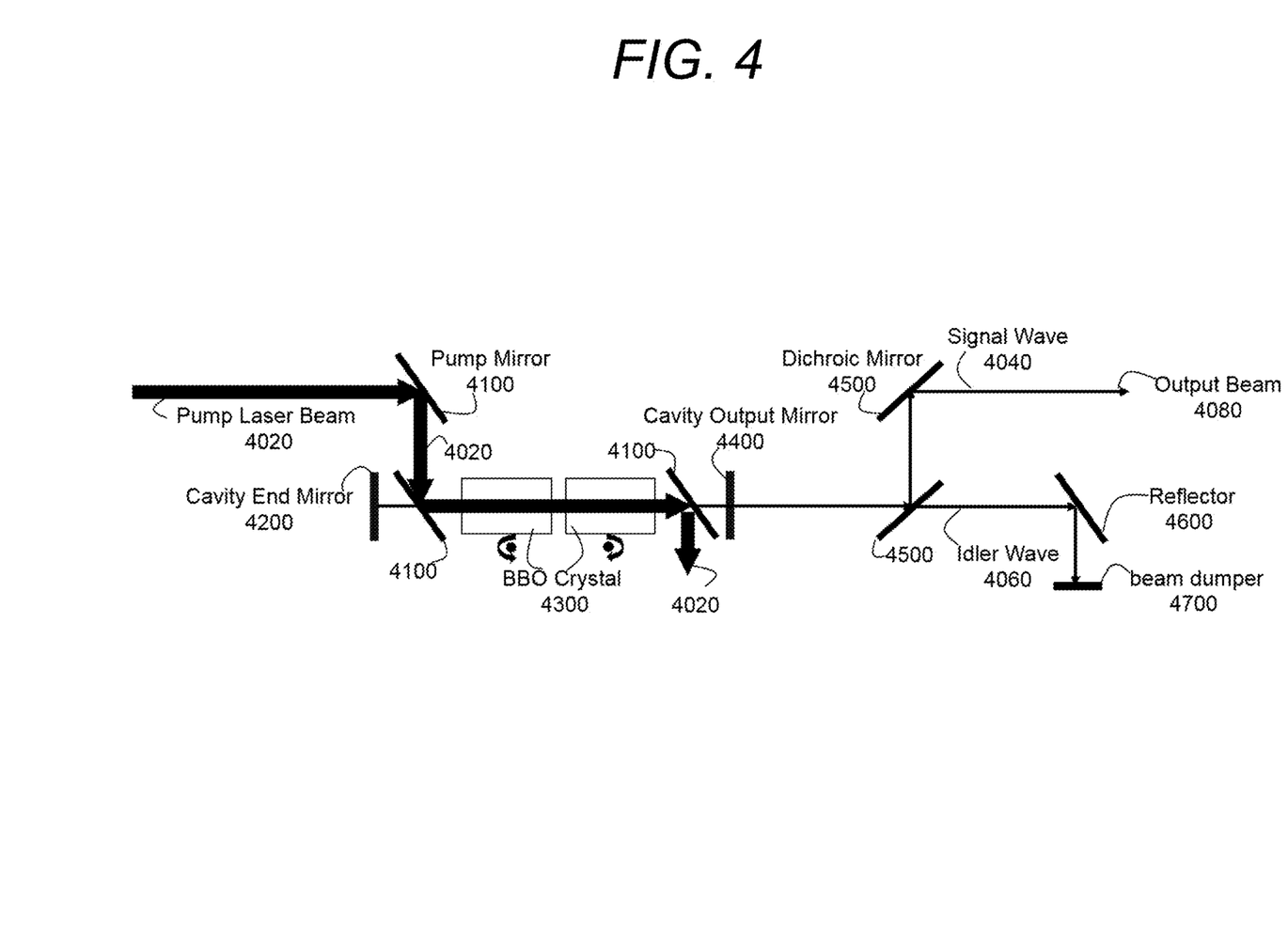
FIG. 4 shows an example of optical parametric oscillator module shown in FIG. 3.

FIG. 4 details an example of the optical parametric oscillator module 3200 of FIG. 3. Three pump mirrors 4100 inject pump laser beam 4020 into the optical parametric oscillator cavity comprising a cavity end mirror 4200, two BBO crystals 4300 and a cavity output mirror 4400. The insertion of pump laser beams 4020 into the oscillator cavity without causing damages on both the cavity end mirror 4200 and cavity output mirror 4400 simplifies the designs of both cavity mirrors 4200 and 4400. The cavity output mirror 4400 outputs partial signal and idler wave and reflects the rest back to oscillator cavity for oscillation. The cavity end mirror 4200 is highly reflective for both signal wave and idler wave in a dual-resonant oscillator (DRO) design. A pair of dichroic mirrors 4500 are used to separate the signal wave 4040 and idler wave 4060. The output beam 4080 can be selected from the signal wave 4040 and idler wave 4060 by a moveable reflector 4600 that deflects the unselected beam, which is the idler beam in this example, to a beam dumper 4700. In this example, both OPO crystals are cut with type-I phase matching with 355 nm pump laser. But the appropriate orientation of the two BBO crystals relative to each other allows the compensation of birefringence walk-off and improvement of conversion efficiency. The tuning of wavelengths of the signal and the idler waves is achieved by rotation of the first BBO crystal and the second BBO crystal around the axes (identified by the black dots below the crystals) below the crystal along anti-clock-wise and clock-wise directions respectively. Modifications such as double-pass of pump laser beams through the OPO crystals or a better ring cavity design may reduce pump threshold, extract more laser energy out of oscillator, and allow higher conversion efficiency. It is understandable that the purpose of this example is to demonstrate that this invention is practical, not to include all possible OPO technique features. Dividing high power pump energy and utilizing multiple parallel optical parametric oscillator modules are keys to overcome technique limitations in prior arts of high power optical parametric oscillator.

Figure 5:
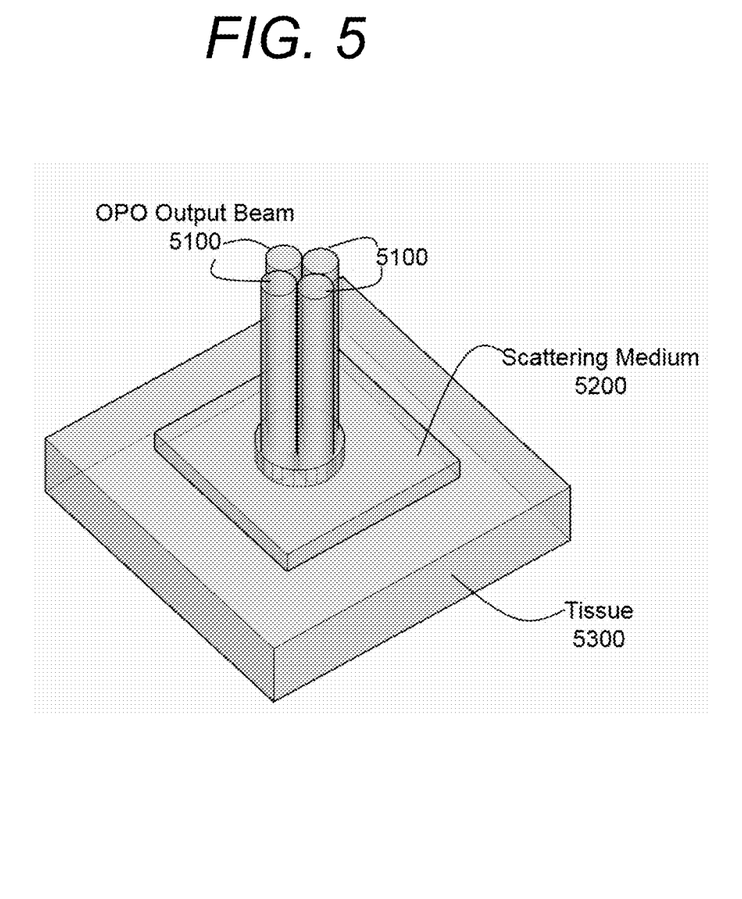
FIG. 5 shows an example of a patient interface that comprises a scattering medium for combining and dispersing multiple output beams on tissue surface for SP laser surgeries with known laser parameters.

As shown in FIG. 1, a laser delivery unit 1300 assembles OPO laser beams 1040, adjusts diameters of the OPO laser beams 1040, delivers the OPO laser beams 1040 with an articulated arm or with an optical light-guide including optical fibers, passes the OPO laser beams 1040 through a patient interface, and illuminates a tissue surface region with laser influences that match with SP applications. For cases when the optimal laser treatment parameters are already known from methods disclosed in U.S. Ser. No. 15/881,748, a simple patient interface as shown in FIG. 5 can combine energies of OPO laser beams 1040, and disperse the combined laser energies onto a tissue surface. In this simple patient interface, multiple OPO output beams 5100 illuminate tissue 5300 surface through a certain thickness of scattering medium 5200. The scattering medium 5200 has a minimum optical absorption to light in VIS-NIR wavelength range and a high transmission to OPO output beams 5100. Thus, most energy of OPO output beams is dispersed onto a circular area on tissue surface with a diameter of several millimeters (mm). The scattering medium 5200 can be conventional optical diffusers, such as ground glass, engineered diffusers or holographic diffusers with high transmission. The scattering medium 5200 can also be any form of high-transmission light guide filled with liquid, solid or gel scattering phantoms containing light scattering particles, with size comparable to wavelengths of visible light. It is preferable that the scattering medium 5200 can pass 80-90% of light energy when it disperses the laser beams. Monte Carol simulation of light transport through the scattering phantom or experimental methods can optimize scattering phantom parameters including the phantom thickness, particle concentration, particle size, light loss, and illuminated area. Conventional optical simulation or experimental methods can be used for the optimized design of conventional optical diffusers. The utilization of a scattering medium to combine laser energies of multiple output beams for demanding SP applications is another key of this invention.

Figure 6:
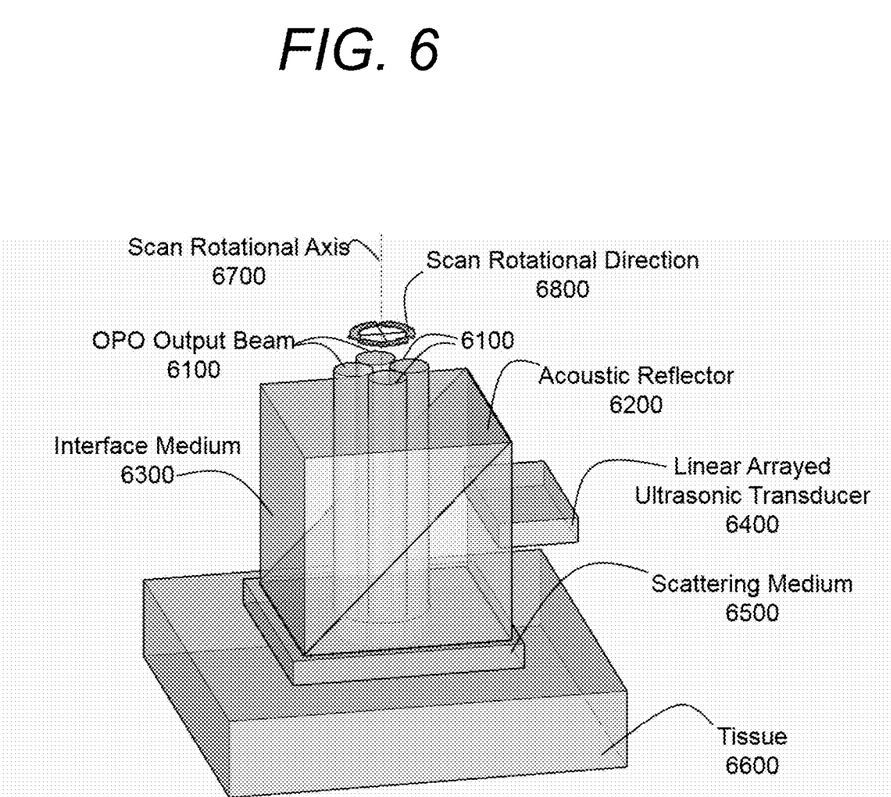
FIG. 6 shows another example of a patient interface that allows acquiring tissue responses and optimal laser parameters with an acoustic detector, combining multiple output beams and dispersing combined energies on tissue surface by a scattering medium.

FIG. 6 shows a general patient interface that allows the acquisition of optimal treatment laser parameters and laser treatment with optimal laser parameters. This general patient interface comprises an acoustic wave reflector 6200, an interface media 6300, a linear arrayed ultrasonic transducer 6400, and a scattering medium 6500 between the interface medium 6300 and tissue 6600. The interface medium 6300 and the acoustic reflector 6200 are transparent to the OPO output beams 6100 while the scattering medium 6500 combine and disperse the OPO output beams 6100 onto a circular area on tissue 6000 surface after the OPO output beams 6100 pass through the scattering medium 6500 with high transmission. The pigmented lesions embedded in tissue are treated by the OPO output beams 6100 upon absorption of laser pulse energy. The pigmented lesions can also generate photoacoustic waves upon the excitation of the OPO output beams 6100. The photoacoustic waves travel upward through the scattering medium 6500 and interface medium 6300 before being reflected by the acoustic reflector 6200 and detected by the linear arrayed ultrasonic transducer 6400. The acoustic impedances of interface medium 6300, scattering medium 6500 and tissue 6600 are preferable to be close in order to minimize loss of photoacoustic waves before the photoacoustic waves are detected by the linear arrayed ultrasonic transducer 6400. When the acoustic reflector 6200 and the linear arrayed ultrasonic transducer 6400 are static, only two-dimensional tissue information beneath the illuminated tissue 6000 surface area can be acquired for the acquisition of optimal laser parameters. When a rotational stage (not shown in FIG. 6) that mounts the acoustic reflector 6200 and the linear arrayed ultrasonic transducer 6400 and rotates them around the scan rotational axis 6700 along scan rotational direction 6800, a three-dimensional tissue information beneath the illuminated tissue 6000 surface area can be acquired for the acquisition of optimal laser parameters. Optimal laser treatment parameters can be applied for the optimized laser treatment thereafter.

Techniques, apparatus and methods for a high power tunable optical parametric oscillator for demanding selective photothermolysis applications such as laser tattoo removal are disclosed. However, variations and enhancements of the described implementations, and other implementations can be made based on what is described.

REFERENCES CITED

U.S. Patent Documents

U.S. Pat. No. 6,607,523 B1 Filed December 2001 by Asah et al.
U.S. Pat. No. 6,723,090 B2 Filed July 2002 by Altshuler et al.
U.S. Pat. No. 6,766,187 B1 Filed September 2000 by Black et al.
U.S. Pat. No. 5,390,211 Filed in August 2093 by Clark et al.
U.S. Pat. No. 7,036,516 B1 Filed August 2098 by Dees et al.
U.S. Pat. No. 5,619,517 Filed in February 2095 by Dixon et al.
U.S. Pat. No. 6,270,492 B1 Filed September 2099 by Edward L. Sinofsky.
U.S. Pat. No. 6,273,883 B1 Filed April 2097 by Furumoto et al.
U.S. Pat. No. 5,117,126 Filed in June 2090 by Geiger et al.
U.S. Pat. No. 7,179,253 B2 Filed March 2004 by Graham et al.
U.S. Pat. No. 7,331,953 B2 Filed April 2005 by Manstein et al.
U.S. Pat. No. 8,394,359 B1 Filed March 2012 by Michael P. O'Neil.
U.S. Pat. No. 6,554,825 B1 Filed May 2000 by Murray et al.
00RE36634 Filed December 2091 by Shahriar Ghaffari et al.
2013/0345685 A1 Filed May 2013 by Poran et al.
Ser. No. 15/881,748 Filed in January 2018 by Rao Bin.
U.S. Pat. No. 7,713,265 B2 Filed December 2006 by Robert J. Dunki-Jacobs.
U.S. Pat. No. 5,879,346 Filed December 2096 by Waldman et al.
U.S. Pat. No. 5,759,200 Filed September 2096 by Zion Azar.

Foreign Patent Documents

WO 2013/033145A1 Filed in August 2011 by Nikolai et al.

Other Publications

Barua et al., "Laser-tissue interaction in tattoo removal by Q-switched lasers," J Cutan Aesthet Surg 8, 5-8(2015).
Bernstein, "Laser Tattoo Removal," SEMINARS IN PLASTICS SURGERY 21, 175-192(2007).
Ortiz et al., "Port-wine stain laser treatment and novel approaches," Facial Plast Surg 28, 611-620(2012).
Peach et al., "Colour shift following tattoo removal with Q-switched Nd-YAG laser (1064/532)," British Journal of Plastic Surgery 52,482-487(1999).
Walter Koechner. Solid-state Laser Engineering. Springer 2006. Print.
Wenzel, "Current concepts in laser tattoo removal," Skin Therapy Letter 15, 3-5(2010).
http://www.spectra-physics.com/products/hidh-enerdy-pulsed-lasers/primoscan-opo [Accessed 2 May 2018]
http://www.spectra-physics.com/products/hidh-enerdy-pulsed-lasers/basiscan [Accessed 2 May 2018]

What is claimed is:

1. A high power tunable optical parametric oscillator (OPO) system with photoacoustic feedbacks for selective photothermolysis laser surgeries, comprising:
   a pump laser configured to produce multiple spatially separated pump laser beams;
   an OPO unit comprising multiple OPO modules producing multiple spatially separated OPO output beams at a desirable wavelength by adjusting phase matching conditions of nonlinear OPO crystals within said OPO modules according to said photoacoustic responses feedbacks;
   a patient interface configured to be in contact with a tissue comprising
      a scattering medium configured to disperse said OPO output beams onto said tissue surface, and
      an acoustic detector configured to be in acoustic contact with said tissue for acquiring said photoacoustic feedbacks; and
   a laser delivery unit configured to direct said OPO output beams towards said patient interface.

2. An optical parametric oscillator system of claim 1, wherein a pulse duration of OPO output beams is in nanosecond or picosecond regime.

3. An optical parametric oscillator system of claim 1, wherein a pulse duration or a pulse-train duration of OPO output beams is longer than 1 millisecond.

4. An optical parametric oscillator system of claim 1, wherein a pulse energy, a pulse duration, and a pulse-train duration of OPO output beams are adjusted through controlling a pulse energy, a pulse duration, and a pulse-train duration of a pump laser.

5. An optical parametric oscillator system of claim 1, wherein pump laser beams are produced by nonlinear harmonics generations from one or more solid-state fundamental lasers with a Master-Oscillator-Power-Amplifier structure pumped by flash-lamps, arc lamps or high-power laser diodes.

6. An optical parametric oscillator system of claim 1, wherein nonlinear OPO crystals are cut in type I phase matching configuration in OPO modules.

7. An optical parametric oscillator system of claim 1, wherein nonlinear OPO crystals are cut in type II phase matching configuration in OPO modules.

8. An optical parametric oscillator system of claim 1, wherein nonlinear OPO crystals are cut in tangential phase matching configuration in OPO modules.

9. An optical parametric oscillator system of claim 1, wherein pump laser beams pass nonlinear OPO crystals twice.

10. An optical parametric oscillator system of claim 1, wherein each OPO module comprises two nonlinear OPO crystals configured to compensate birefringence walk-off, lower pump threshold energy, and improve conversion efficiency.

11. An optical parametric oscillator system of claim 1, wherein OPO modules share a pair of cavity end mirror and cavity output mirror.

12. An optical parametric oscillator system of claim 1, wherein a scattering medium is an optical diffuser.

13. An optical parametric oscillator system of claim 1, wherein a scattering medium is a light guide filled with liquid, solid or gel scattering phantoms containing light scattering particles.

* * * * *